US011653848B2

(12) United States Patent
Lane et al.

(10) Patent No.: US 11,653,848 B2
(45) Date of Patent: May 23, 2023

(54) VITAL SIGN DETECTION AND MEASUREMENT

(71) Applicant: Welch Allyn, Inc., Skaneateles Falls, NY (US)

(72) Inventors: John A. Lane, Weedsport, NY (US);
Steven D. Baker, Beaverton, OR (US);
Lei Guo, Camillus, NY (US);
Raymond A. Lia, Auburn, NY (US);
Robert L. Vivenzio, Auburn, NY (US);
Ervin Goldfain, Syracuse, NY (US);
Brian T. Moons, Sherwood, OR (US);
Zhengguo Sun, West Henrietta, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 388 days.

(21) Appl. No.: 16/748,293

(22) Filed: Jan. 21, 2020

(65) Prior Publication Data
US 2020/0237252 A1    Jul. 30, 2020

Related U.S. Application Data

(60) Provisional application No. 62/798,124, filed on Jan. 29, 2019.

(51) Int. Cl.
*A61B 5/05*     (2021.01)
*G01S 13/88*    (2006.01)
(Continued)

(52) U.S. Cl.
CPC .............. *A61B 5/05* (2013.01); *A61B 5/0205* (2013.01); *A61B 5/02444* (2013.01);
(Continued)

(58) Field of Classification Search
CPC ..... A61B 5/05; A61B 5/0205; A61B 5/02444; A61B 5/0816; A61B 5/4842;
(Continued)

(56) References Cited

U.S. PATENT DOCUMENTS 2,603,749 A  *  7/1952  Kock ...................... H01P 3/122
                                                  343/756
2,887,684 A  *  5/1959  Dexter ..................... H01Q 3/14
                                                  343/781 R
(Continued)

FOREIGN PATENT DOCUMENTS

EP          2438849 A1    4/2012
WO       2008001092 A2    1/2008
(Continued)

OTHER PUBLICATIONS

Ernst, Robert, "Development of a Compact, Highly Integrated 60GHz FMCW Radar for Human Vital Sign Monitoring ," (Jun. 29, 2016) (Halmstad University Masters Thesis). (Year: 2016).*
(Continued)

*Primary Examiner* — Joel Lamprecht
*Assistant Examiner* — Ashish S Jasani
(74) *Attorney, Agent, or Firm* — Merchant & Gould P.C.

(57) ABSTRACT

A patient monitoring device includes a signal transmission device configured to direct a signal transmission toward a target area and to receive reflected signals from the target area, and a signal analysis device having a processing device and at least one non-transitory computer readable data storage device storing instructions, that when executed by the processing device, cause the patient monitoring device to transmit signals, receive reflected signals, and determine a non-contact vital sign measurement based on data from the reflected signals.

17 Claims, 11 Drawing Sheets

(51) Int. Cl.
*A61B 5/024* (2006.01)
*A61B 5/08* (2006.01)
*A61B 5/00* (2006.01)
*A61B 5/0205* (2006.01)
*A61B 90/00* (2016.01)
*A61B 5/11* (2006.01)
*A61B 5/113* (2006.01)

(52) U.S. Cl.
CPC .......... *A61B 5/0816* (2013.01); *A61B 5/4842* (2013.01); *A61B 5/7275* (2013.01); *A61B 5/7278* (2013.01); *A61B 5/742* (2013.01); *G01S 13/88* (2013.01); *A61B 5/1102* (2013.01); *A61B 5/113* (2013.01); *A61B 5/1127* (2013.01); *A61B 2090/3975* (2016.02)

(58) Field of Classification Search
CPC ..... A61B 5/7275; A61B 5/7278; A61B 5/742; A61B 5/113; A61B 5/002; G01S 13/88; G01S 13/56; G01S 7/032; H01Q 19/062
See application file for complete search history.

(56) References Cited

U.S. PATENT DOCUMENTS

| | | | |
|---|---|---|---|
| 7,119,758 B2* | 10/2006 | Louzir | H01Q 19/062 |
| | | | 343/753 |
| 8,068,053 B1* | 11/2011 | Stutzke | H01Q 3/14 |
| | | | 342/75 |
| 8,761,853 B2 | 6/2014 | Thaveeprungsriporn et al. | |
| 8,977,347 B2 | 3/2015 | Mestha et al. | |
| 9,020,185 B2 | 4/2015 | Mestha et al. | |
| 2007/0060802 A1 | 3/2007 | Ghevondian et al. | |
| 2010/0249630 A1* | 9/2010 | Droitcour | G01S 13/88 |
| | | | 607/42 |
| 2011/0263952 A1 | 10/2011 | Bergman et al. | |
| 2013/0019405 A1 | 1/2013 | Flanagan et al. | |
| 2013/0345568 A1 | 12/2013 | Mestha et al. | |
| 2014/0275833 A1 | 9/2014 | Vanderpohl, III | |
| 2014/0276504 A1 | 9/2014 | Heil et al. | |
| 2014/0303454 A1 | 10/2014 | Clifton et al. | |
| 2015/0201859 A1 | 7/2015 | Baker et al. | |
| 2015/0282724 A1 | 10/2015 | McDuff et al. | |
| 2015/0302158 A1 | 10/2015 | Morris et al. | |
| 2015/0379370 A1 | 12/2015 | Clifton et al. | |
| 2016/0081618 A1* | 3/2016 | Han-Oh | A61B 5/4836 |
| | | | 600/430 |
| 2017/0133754 A1* | 5/2017 | Raeker | H04B 5/0012 |
| 2017/0328997 A1* | 11/2017 | Silverstein | G01S 13/765 |
| 2018/0078216 A1 | 3/2018 | Baker et al. | |
| 2018/0214091 A1* | 8/2018 | Baker | A61B 5/746 |
| 2019/0015277 A1* | 1/2019 | Sauser | G01S 7/032 |
| 2019/0053707 A1* | 2/2019 | Lane | A61B 5/0507 |

FOREIGN PATENT DOCUMENTS

| | | |
|---|---|---|
| WO | 2014030091 A1 | 2/2014 |
| WO | 2014055755 A1 | 4/2014 |
| WO | 2015078735 A1 | 6/2015 |
| WO | 2015086338 A1 | 6/2015 |
| WO | 2016092290 A1 | 6/2016 |
| WO | 2016-123287 A1 | 8/2016 |
| WO | 2019036155 A1 | 2/2019 |

OTHER PUBLICATIONS

Ren et al., "Analysis of Micro-Doppler Signatures for Vital Sign Detection using UWB Impulse Doppler Radar," (Apr. 4, 2016) 2016 IEEE Topical Conference on Biomedical Wireless Technologies, Networks, and Sensing Systems (BioWireleSS), 2016, pp. 18-21, doi: 10.1109/BIOWIRELESS.2016.7445550. (Year: 2016).*

Yi Huan et al: 3-D Printed Millimeter-Wave and Terahertz Lenses Fixed and Frequency Scanned Beam11 , IEEE Transactions On Antennas and Propagation, IEEE Service Center, Piscataway, NJ, US, vol. 64, No. 2, Feb. 1, 2016 (Feb. 1, 2016), pp. 442-449.

Extended European Search Report for Application No. 20154186.9 dated Mar. 24, 2020.

Wu, Hao-Yu et al., "Eulerian Video Magnification for Revealing Subtle Changes in the World," http://people.csail.mit.edu/mrub/papers/vidmag.pdf, Jul. 4, 2012, 8 pages.

Tarassenko, L. et al., "Non-contact vide-based vital sign monitoring using ambient light and auto-regressive models," http://iopscience.iop.org/article/10.1088/0967-3334/35/5/807/meta, Institute of Physics and Engineering in Medicine, 2014, 26 pages.

Chandler, David L., "Your vital signs, on camera," http://news.mit.edu/2010/pulse-camera-1004, Oct. 4, 2010, 3 pages.

Iovescu, C. et al., "The fundamentals of millimeter wave sensors," Texas Instruments, May 2017, 9 pages.

* cited by examiner

VITAL SIGN DETECTION AND MEASUREMENT

BACKGROUND

Trained medical professionals often check vital sign measurements of a patient under their care at regular intervals to monitor the status of the patient. One vital sign that is monitored is respiration rate. Respiration rate is the number of breaths a person takes per minute. The rate is usually measured when a person is at rest and involves counting the number of breaths per minute. In addition, the quality and depth of respiration such as shallow breathing or labored breathing, and the uniformity of breath may be monitored by a trained medical professional.

Measuring the respiration rate of a patient can be difficult because, unlike other vital signs that can be measured by using devices connected to the patient and that use automated processes, respiration rate is still often measured by hand (e.g., by counting how many times the chest of the patient moves up and down while breathing for a period of time). Additionally, respiration rate is slower compared to other vital signs (e.g., a normal respiration rate for an adult at rest is 12 to 20 breaths per minute) and is difficult and cumbersome to measure by hand.

SUMMARY

In general terms, the present disclosure relates to a patient monitoring device and method. In one possible configuration and by non-limiting example, the device and method determine a vital sign measurement without physically contacting a patient. Various aspects are described in this disclosure, which include, but are not limited to, the following aspects.

In one aspect, a patient monitoring device has a signal transmission device configured to direct a signal transmission toward a target area and to receive reflected signals from the target area and a signal analysis device having a processing device and at least one non-transitory computer readable data storage device storing instructions, that when executed by the processing device, cause the patient monitoring device to transmit signals, receive reflected signals, and determine a non-contact vital sign measurement based on data from the reflected signals.

In another aspect, a patient monitoring device includes a signal transmission device configured to direct a radar signal transmission toward a target area and to receive reflected radar signals from the target area; and a signal analysis device programmed to determine a respiration rate based on data from the reflected radar signals.

In another aspect, a method of acquiring a vital sign measurement comprises transmitting signals toward a target area; receiving reflected signals; adjusting a direction of the signal transmission; adjusting a focus of the signal transmission; and determining a vital sign measurement based on data from the reflected signals.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
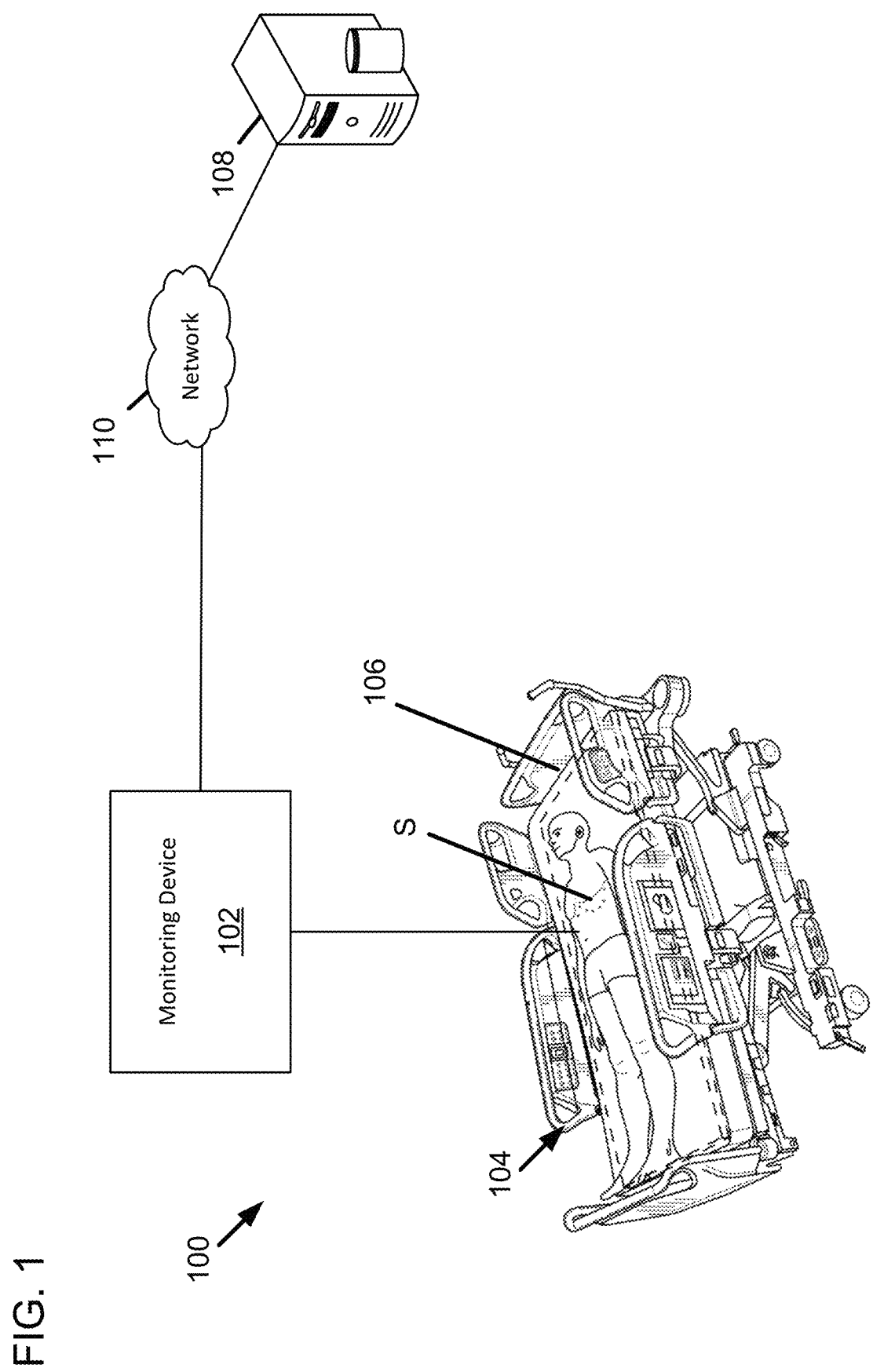
FIG. 1 schematically illustrates an example patient monitoring system.

FIG. 1 schematically illustrates an example patient monitoring system 100. As shown in FIG. 1, the patient monitoring system 100 includes a monitoring device 102 configured to determine and display one or more vital signs of a subject S located in a subject arrangement area 104. In this example, the vital signs are obtained noninvasively, without having to touch or contact the subject S. The vital signs may be displayed numerically, in waveform, in tabular data, in plots of tabular data, and the like.

The subject S is a person, such as a patient, who is clinically treated by one or more medical professionals. As shown in FIG. 1, the subject S is arranged in the subject arrangement area 104, which can be located inside a healthcare facility such as a hospital, medical clinic, doctor's office, etc. The subject arrangement area 104 can include a support device 106, such as a bed, on which the subject S can lie, rest, or sleep. Other examples of the support device 106 include lifts, chairs, stretchers, and surgical tables.

In some examples, the monitoring device 102 is operable to communicate with a data management system 108 via a data communication network 110. The data management system 108 operates to manage personal and/or medical information, such as health conditions and other information of the subject S. The data management system 108 can be operated by medical professionals or healthcare service providers.

The data management system 108 communicates with the monitoring device 102. For example, the monitoring device 102 and the data management system 108 are connected via the network 110 to transmit data such as measured vital signs and other data associated with the subject S. In some examples, the monitoring device 102 is capable of directly communicating with the data management system 108. The data management system 108 operates to provide information that can be used to assist trained medical professionals to provide suitable healthcare to the subject S. Examples of the data management system 108 include Connex® data management systems available from Welch Allyn Inc., Skaneateles Falls, N.Y. The data management system 108 may provide a connection to electronic medical record or electronic health record servers. Alternatively, the data management system 108 may itself be an electronic medical record server or an electronic health record server.

The data communication network 110 communicates data between one or more computing devices, such as among the monitoring device 102 and the data management system 108. Examples of the network 110 include a local area network and a wide area network, such as the Internet. In some examples, the network 110 includes a wireless communication system, a wired communication system, or a combination of wireless and wired communication systems. A wired communication system can transmit data using electrical or optical signals in various possible configurations. Wireless communication systems typically transmit signals via electromagnetic waves, such as in the form of optical signals or radio frequency (RF) signals.

A wireless communication system can include an optical or RF transmitter for transmitting optical or RF signals, and an optical or RF receiver for receiving optical or RF signals. Examples of wireless communication systems include Wi-Fi communication devices that utilize wireless routers or wireless access points, cellular communication devices that utilize one or more cellular base stations, Bluetooth, ANT, ZigBee, medical body area networks, personal communications service (PCS), wireless medical telemetry service (WMTS), and other wireless communication devices and services.

Figure 2:
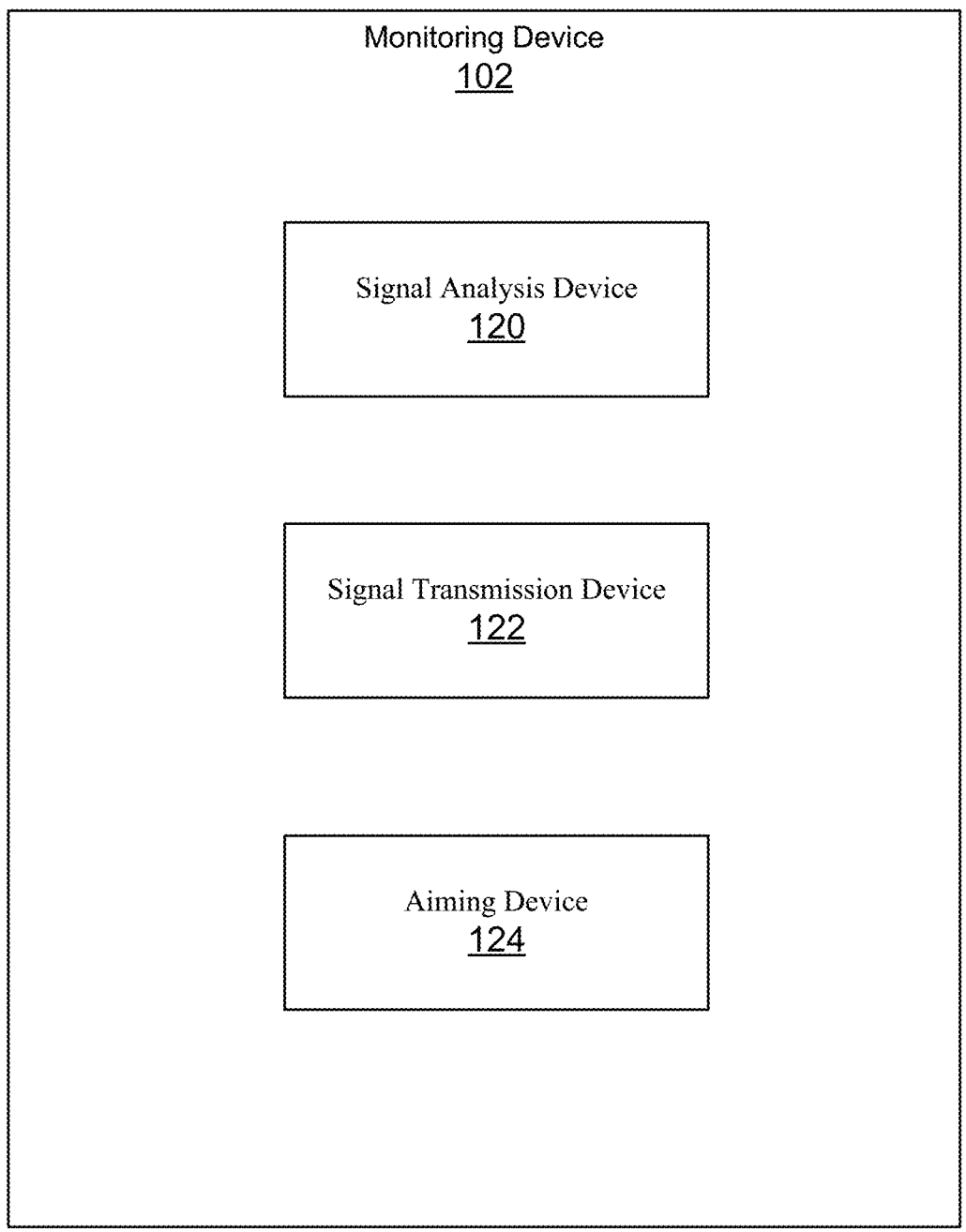
FIG. 2 schematically illustrates an example monitoring device.

FIG. 2 illustrates an example of the monitoring device 102. The monitoring device 102 includes a signal analysis device 120, a signal transmission device 122, and an aiming device 124. In certain examples, the signal transmission device 122 and the aiming device 124 are attached to an external housing of the monitoring device 102, and the signal analysis device 120 is a hardware component of the monitoring device. In some examples, the monitoring device 102 is a Connex® spot monitor available from Welch Allyn Inc., Skaneateles Falls, N.Y.

The signal transmission device 122 operates to detect a vital sign of the subject S arranged in the subject arrangement area 104. In one example, the signal transmission device 122 includes a radar signal transceiver to transmit radar signals toward the subject S and receive reflected radar signals, which can be used to determine the vital sign measurement. In other examples, LIDAR, ultrasound, sonar, and the like may be used. In certain examples, the signal transmission device 122 includes an antenna. An example configuration of the signal transmission device 122 is described in more detail with reference to FIGS. 3-5.

The signal analysis device 120 operates to analyze the radar signals received from the signal transmission device 122 and determine a vital sign measurement. The signal analysis device 120 includes a processing device and at least one non-transitory computer readable data storage device storing instructions executable by the processing device. In some examples, the signal analysis device 120 is integral with the signal transmission device 122. Various methods used in the signal analysis device 120 and signal transmission device 122 are described herein.

The aiming device 124 is configured to visually indicate the direction of the radar signals transmitted from the signal transmission device 122. For example, the aiming device 124 can be a laser or a light-emitting diode (LED) that emits a visible light in the direction of the radar signals transmitted from the signal transmission device 122. In this manner, the aiming device 124 assists a medical professional to direct the signal transmission device 122 towards an appropriate target area (e.g., the subject arrangement area 104 where the subject S is located), and even more specifically towards a specific anatomical area of the subject S such as the chest of the subject S. The visible light emitted from the aiming device 124 not only ensures that the signal transmission device 122 is pointed in an appropriate direction, but also provides a visual confirmation to a medical profession that data is being collected.

Figure 3:
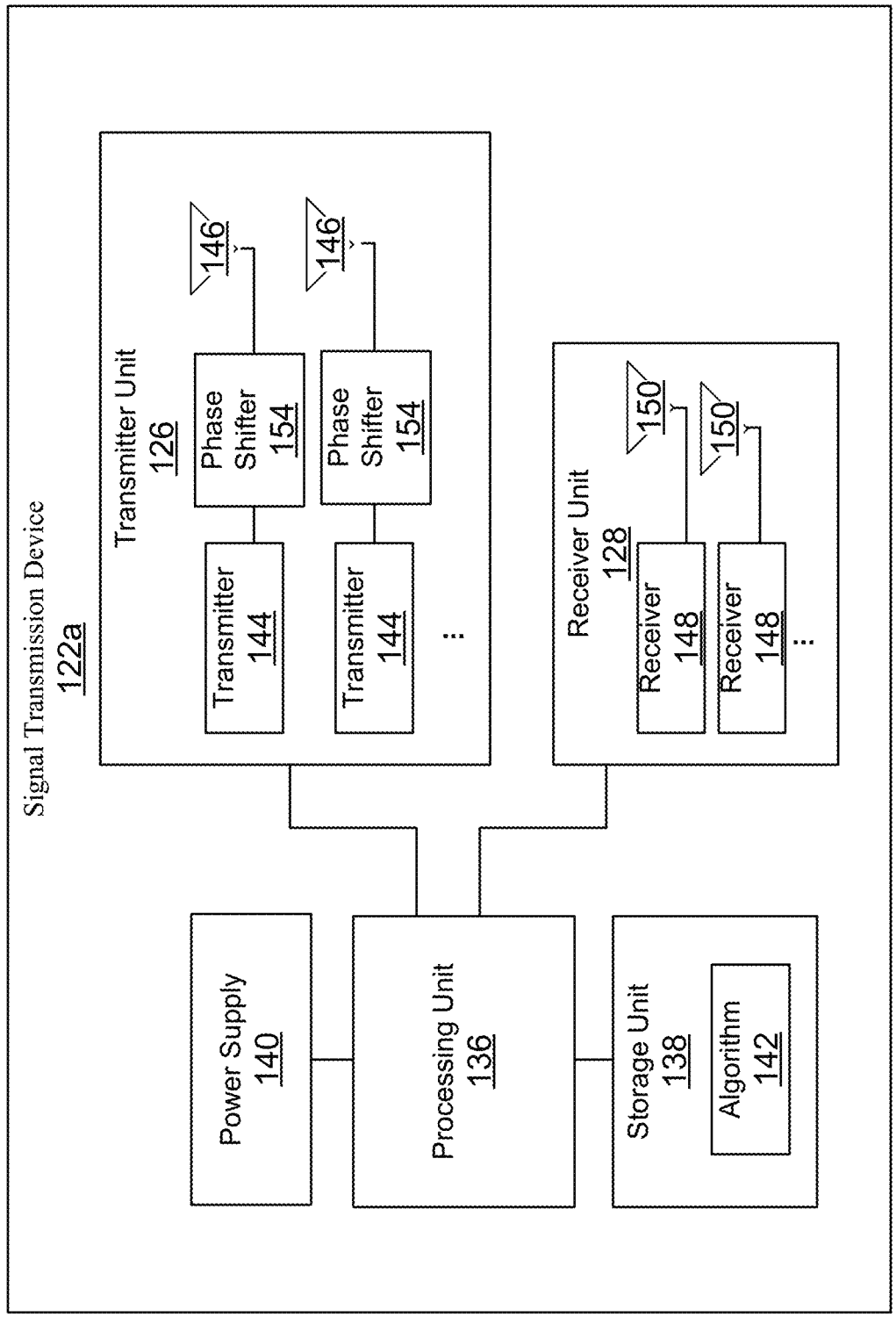
FIG. 3 schematically illustrates an example signal transmission device.

FIG. 3 illustrates an example configuration of a signal transmission device 122a. In this example, the signal transmission device 122a includes a transmitter unit 126, a receiver unit 128, a processing unit 136, a storage unit 138, and a power supply 140. In certain aspects, these components are similar to the components described in U.S. patent application Ser. No. 15/679,570 filed on Aug. 17, 2017, the entirety of which is hereby incorporated by reference.

The signal transmission device 122a is configured as a radar module that uses radar signals to determine various characteristics of objects. For example, range and velocity are used to infer characteristics such as whether an object is accelerating or decelerating or if an object is rotating. Combinations of these motions are used to characterize the activity of the object. For example, the signal transmission device 122a is configured to detect one or more vital signs of the subject S, as described herein. In some examples, the signal transmission device 122a is configured to incorporate at least some functionalities of the signal analysis device 120.

The transmitter unit 126 includes one or more signal transmitters 144 for producing radar signals, and one or more transmitting antennas 146 for transmitting the radar signals toward a target area such as the subject arrangement area 104 where the subject S is located (see for example FIG. 1). Other examples may use the same antenna(s) for transmission and reception. The radar signals transmitted from the transmitting antennas 146 reflect off objects (such as the subject S and surrounding objects in the subject arrangement area 104) and return to the receiver unit 128. For example, the signal transmitters 144 emit radar signals (also referred to as radio waves or electromagnetic waves) in predetermined directions through the transmitting antennas 146. In some examples, signal transmitters 144 use pulsed frequency chirping to emit radar signals at predetermined time intervals. In certain examples, signal transmitters 144 use frequency chirping to emit radar signals at predetermined time intervals of 50 milliseconds. When the radar signals come into contact with objects, the radar signals are reflected or scattered in many directions, with some radar signals reflected back towards the receiver unit 128.

The receiver unit 128 includes one or more signal receivers 148 and one or more receiving antennas 150 for receiving the radar signals reflected from objects such as the subject S. In some examples, the same antennas can be used for both the receiving antennas 150 and the transmitting antennas 146. In other examples, the receiver unit 128 is arranged in the same location as, or adjacent to, the transmitter unit 126. In certain examples, the reflected signals captured by the receiving antennas 150 can be strengthened by electronic amplifiers and/or signal-processed to recover useful radar signals.

A plurality of signal transmitters 144, a plurality of transmitting antennas 146, a plurality of signal receivers 148, and a plurality of receiving antennas 150 can be used to transmit signals to different directions or angles, and receive reflected signals from different directions or angles, thereby detecting different objects and/or different portions of a single object, which can be used to map different objects and/or different portions of an object within a target area that is being monitored by the signal transmission device 122a. In certain examples, the antenna direction may be manually adjusted.

The reflected radar signals received by the receiver unit 128 are delayed versions of the radar signals transmitted from the transmitter unit 126. The radar signals that are reflected back towards the receiver unit 128 can be used to measure a vital sign of the subject S such as by monitoring changes in the frequency of the radar signals, caused by the Doppler effect, due to an object moving toward or away from the signal transmission device 122a and to measure the range, caused by the delay in the received signal. In some examples, the scale of the movement is small and the effect is termed micro-Doppler effect. The terms Doppler effect and micro-Doppler effect are used interchangeably. For example, the detected range and Doppler frequency of the radar signals caused by the chest of the subject S moving up and down during breathing can be measured to determine a respiration rate and a depth of respiration of the subject S. In this manner, the phase of the reflected radar signals can be monitored to measure one or more vital signs of the subject S without having to contact the subject S.

Various types of radar signals can be used by the signal transmission device 122a. In one example, the signal transmission device 122a uses millimeter waves (also referred to as mmWaves or millimeter band), which are in the spectrum between about 30 GHz and about 300 GHz. Millimeter waves are also known as extremely high frequency (EHF) waves. Millimeter waves have short wavelengths that can range from about 10 millimeters to about 1 millimeter.

Still referring to FIG. 3, the processing unit 136 operates to control the transmitter unit 126 and the receiver unit 128. In some examples, the processing unit 136 is further configured to perform the functionalities of the signal analysis device 120, such as processing and analyzing of the radar signals to determine a vital sign measurement of the subject S.

The storage unit 138 includes one or more memories configured to store data associated with the radar signals and data usable to evaluate the radar signals. The storage unit 138 can be of various types, including volatile and nonvolatile, removable and non-removable, and/or persistent media. In some embodiments, the storage unit 138 is an erasable programmable read only memory (EPROM) or flash memory.

The power supply 140 provides power to operate the signal transmission device 122a and associated elements. In some examples, the power supply 140 includes one or more batteries, which is either for single use or rechargeable. In other examples, the power supply 140 includes an external power source, such as mains power or external batteries.

As shown in FIG. 3, the signal transmission device 122a is a phased array that electronically adjusts the direction and focus of the radar signal transmission. In this example, the storage unit 138 stores an algorithm 142 that uses the amplitude of the reflected radar signals to electronically adjust the direction and focus of the radar signal transmission. Alternatively, the algorithm 142 may be stored in a memory of the signal analysis device 120. The algorithm 142, when executed by the processing unit 136, causes the processing unit 136 to electronically steer the transmitting antennas 146 to adjust the direction of the radar signal transmission in the azimuth and elevation directions. Additionally, the algorithm 142 causes the processing unit 136 to electronically focus the radar signal transmission by narrowing the dispersion of the radar signals (e.g., from 120 degrees to 40 degrees, 30 degrees, 20 degrees, etc.) to increase the density of the radar signals on a target area.

In the example of FIG. 3, the radar signals produced from the signal transmitters 144 are fed to the transmitting antennas 146 through phase shifters 154, controlled by the processing unit 136, which alter the phase of the radar signals electronically, to steer the radar signals to different directions. The algorithm 142 also adjusts the focus of the radar signals transmitted from the transmitting antennas 146 by controlling the dispersion of the radar signals in a particular direction. Electronically controlling the direction and focus of the radar signals emitted from the transmitting antennas 146 reduces noise and improves the signal strength. In addition to the example in FIG. 3, the phase shifter 154 may also be incorporated in the receiver unit 128.

As desired above, one example target area for the radar signal transmission is the torso of the subject S. In this example, the algorithm 142 when executed by the processing unit 136 not only causes the signal transmission device 122a to direct the transmission of the radar signals on the torso, but also causes the signal transmission device 122a to focus the transmission of the radar signals on a particular area on the torso. For example, the algorithm 142 can direct the signal transmission device 122a to focus the radar signal transmission on the chest of the subject S. By using the Doppler effect as described above, a change in the frequency of the reflected radar signals that result from the chest of the subject S moving up and down during breathing can be monitored by the signal transmission device 122a to determine a respiration rate of the subject S. A depth of respiration of the subject S can also be measured by the signal transmission device 122a by monitoring the delay of the reflected radar signals. Inhalation and exhalation may also be detected by determining whether the delay is increasing or decreasing. Because of the small motion relative to a wavelength, the delay may be detected as a phase shift.

In examples where a low signal-to-noise ratio is detected, the signal analysis device 120 uses the algorithm 142 to steer the transmission of the radar signals elsewhere, for example, towards the abdomen (e.g., stomach) of the subject S. In further examples where the subject S is a belly breather, which is also known as abdominal breathing or diaphragmatic breathing, and which causes the stomach of the subject S to expand as the subject S inhales, the signal analysis device 120 uses the algorithm 142 to steer the signal transmission device 122a in a direction to focus the transmission of the radar signals on a different area of the torso such as the abdomen of the subject S for measuring respiration rate. In some examples, the signal analysis device 120 uses the algorithm 142 to steer the signal transmission device 122a to focus the transmission of the radar signals on two target areas simultaneously, such as the chest and abdomen of the subject S, and the signal transmission device 122a uses time multiplexing between the two target areas to measure the respiration rate of the subject S more accurately.

Additionally, the algorithm 142 can be used by the signal transmission device 122a to focus the transmission of the radar signals on other target areas of the torso of the subject S, such as an area between the ribs at which the apex of the heart pushes. By focusing the transmission of radar signals on this area of the ribs and by using the Doppler effect as described above, the heart rate of the subject S can be determined. Alternatively, ranging methods, including those associated with chirped radar pulses, may be used to determine the heart rate of the subject S.

In one example embodiment, the signal transmission device 122a, when performing the algorithm 142, scans a wide field of view such as a room where the subject S is located. For example, the field of view scanned by the signal transmission device 122a can be 120 degrees or greater. When a signal representative of a vital sign is detected in the field of view, the algorithm 142 automatically focuses the radar signal transmission from the signal transmission device 122a by narrowing the field of view on the target area where the signal is detected. This can improve the signal quality and reduce noise. Thereafter, the signal transmission device 122a can monitor the detected signal to determine a vital sign measurement.

In some examples, the algorithm 142 can be used to distinguish between different subjects in the wide field of view (e.g., 120 degrees) of the signal transmission device 122a. In an example scenario, a patient such as the subject S is in a bed with relatively little motion, and a nurse is present in the patient's room and is ambulate (e.g., moving from place to place within the room). A band-pass Doppler filter is used to select the output of the radar to ignore objects that move above a certain velocity and to ignore objects that are motionless. A clutter filter may also be used to subtract background objects. The radar can scan and track multiple people in the patient's room and ignore those who ambulate, such as the nurse. Filters may also be designed that selectively allow known respiration models, which include depth, rate, overall rhythm, inhalation to exhalation time, slope of the inhalation curve, slope of the exhalation curve, and time in a relaxed state between exhalation and inhalation. Once the target range of the patient is known, data from that range including nearby range gates is collected. Sudden range changes can be ignored, for example, when a person or object is moved between the antenna and the target, and the radar continues to attempt to range the target at the prior range. Similarly, the patient is expected to move relatively slowly, the target's azimuthal and elevation angles from the antenna are expected to change slowly, so sudden changes to the location of the strongest received signal may be ignored (or may be used to trigger a new targeting cycle). Matched filters may also be used to detect valid respiration signals, and this detection is used as positive feedback and the optimal direction of the phased-grid array antenna may be obtained by maximizing this signal over the range of azimuth and elevation angles. Other methods of detecting valid respiration such as machine learning and pattern recognition may also be used.

In addition to the foregoing methods, an area can be scanned for identifying a specific patient within the area by placing a tag on the patient to act as a "beacon" so that the signal transmission device 122a can identify the correct patient and set of vitals within the area. In this example, the tag can emit IR light, video, NFC, RF, or low frequency sound as a beacon or source signal that is detected by the signal transmission device 122a.

Figure 4:
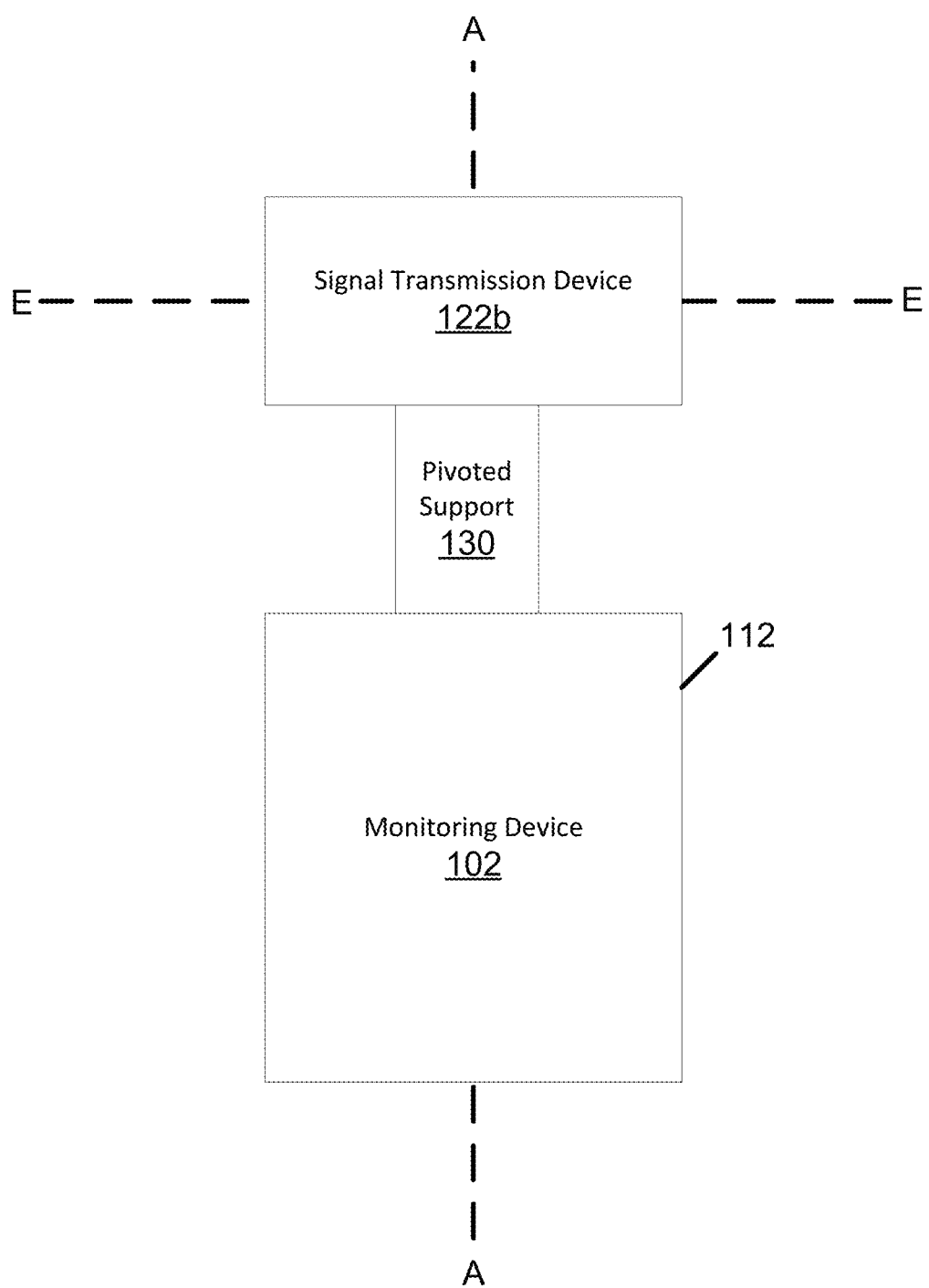
FIG. 4 illustrates another example signal transmission device.
Figure 5:
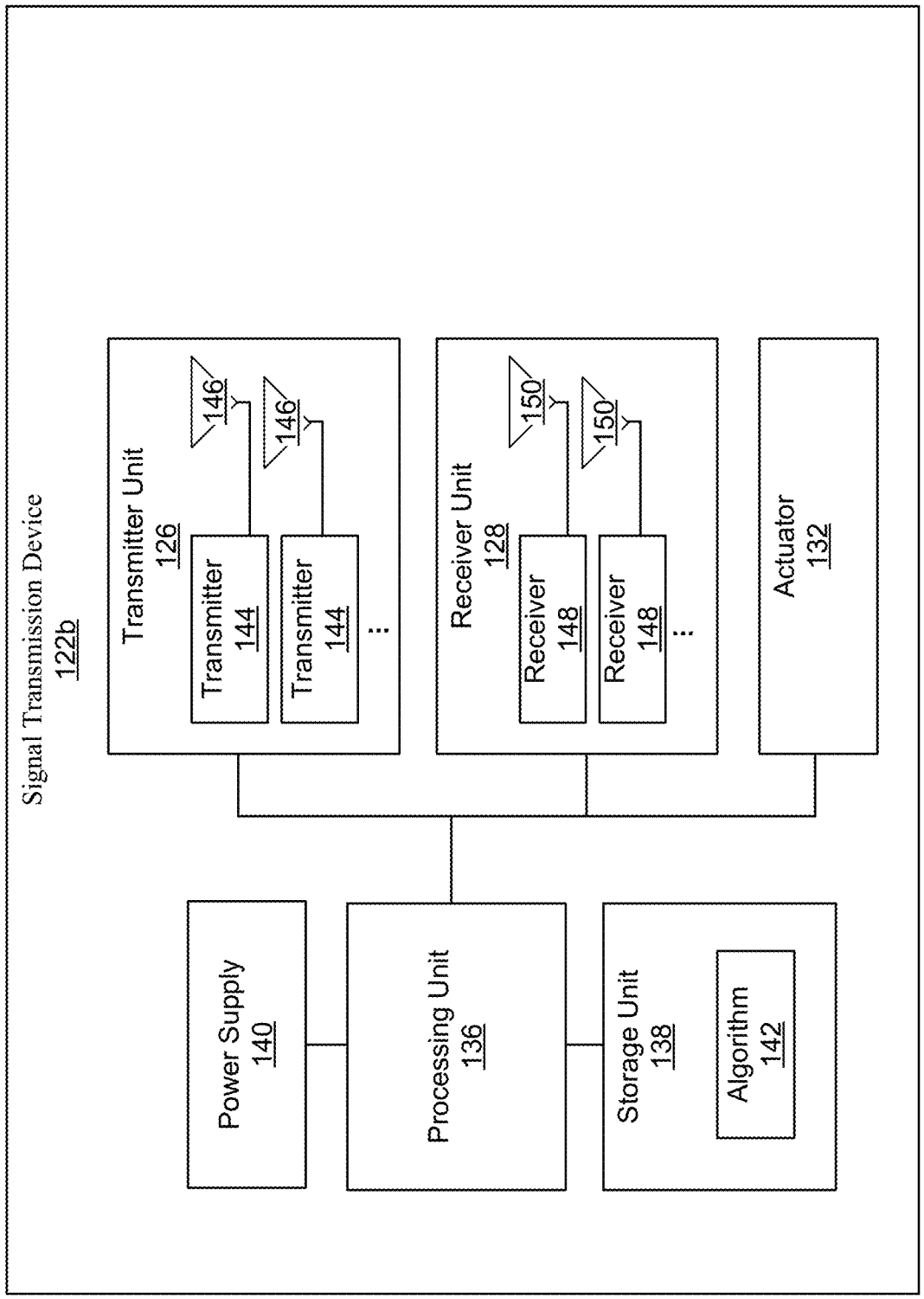
FIG. 5 schematically illustrates the example signal transmission device of FIG. 4.

FIGS. 4 and 5 illustrate another example configuration of a signal transmission device 122b that uses automatic target recognition (ATR) to mechanically steer the signal transmission device 122b. The signal transmission device 122b is similar to the signal transmission device 122a described above and utilizes similar workflows such as to distinguish between different subjects in the wide field of view of the signal transmission device 122b. The signal transmission device 122b includes a transmitter unit 126, a receiver unit 128, a processing unit 136, a storage unit 138, and a power supply 140, and is configured as a radar module that uses radar signals to determine various characteristics of objects such as one or more vital signs of the subject S, as described herein.

As shown in FIG. 4, the signal transmission device 122b is attached to an exterior housing 112 of the monitoring device 102 by a pivoted support 130. In certain examples, the pivoted support 130 is a gimbal or gyroscope. The pivoted support 130 allows the signal transmission device 122b to be rotated about an azimuth axis A-A and an elevation axis E-E.

Referring now to FIG. 5, the storage unit 138 stores the algorithm 142 that is used by the signal transmission device 122b to recognize and track the movement of a target area based on data obtained from the reflected radar signals. Alternatively, the algorithm 142 may be stored in a memory of the signal analysis device 120. In some examples, the algorithm used by the signal transmission device 122b is different from the algorithm used by the signal transmission device 122a. In some examples, the algorithm used by the signal transmission device 122b is the same as the algorithm used by the signal transmission device 122a.

As shown in FIG. 5, the transmitter unit 126 includes one or more signal transmitters 144 for producing radar signals, and one or more transmitting antennas 146 for transmitting the radar signals toward a target area. Data from the reflected radar signals is received by the receiver unit 128 that includes one or more signal receivers 148 and one or more receiving antennas 150 for receiving the radar signals reflected from objects such as the subject S.

The data from the reflected radar signals is used by the algorithm 142 to detect a signal and identify a target area (e.g., the chest of the subject S). When a signal and target area are detected, the algorithm 142, when executed by the processing unit 136, causes the processing unit 136 to drive an actuator 132 to mechanically steer the pivoted support 130. The signal transmission device 122b can be mechanically steered about the azimuth axis A-A and the elevation axis E-E (see FIG. 4) so that the signal transmission device 122b is pointed in the direction of the target area to reduce noise and improve signal strength.

In some examples, the data from the reflected radar signals is monitored and the processing unit 136 uses the algorithm 142 to track a movement of the target area such that when the subject S moves in or out of the support device 106, the signal transmission device 122b is mechanically steered so that it remains pointed in the direction of the target area to reduce noise and maintain signal strength even when the subject S moves.

In some examples, the signal transmission device 122b uses feature vectors to identify the target area. A feature vector is a property or characteristic that can be measured. For example, a feature vector is a one-dimensional matrix used to describe a measured property or characteristic such as the thoracic motion that describes inhalation, rest, exhalation, and rest. More detailed feature vectors allow detection of different depths and rates of respiration, and for detection of respiratory features that indicate ailments such as rales (which are abnormal lung sounds characterized by discontinuous clicking or rattling sounds) and stridor (which is a high-pitched, wheezing sound caused by disrupted airflow). Because the signal is slowly varying, the automatic target recognition of the signal transmission device 122b may include both time-domain (e.g. matched filters) and frequency domain (fast Fourier transform, fast Hartley transform, short fast Fourier transform) analysis. Additionally, mixed domain analysis processing and filters (e.g. wavelets, Gabor transform, Wigner Distribution Function) may be used. Once the target information has been extracted, it can be compared to known target profiles in an existing database that will identify what the target is, for example, cardiac or respiratory signal, as well as the rate of the signal. Alternately, a weighting algorithm may be used to weight the importance of each detected feature as part of a classification algorithm.

Figure 6:
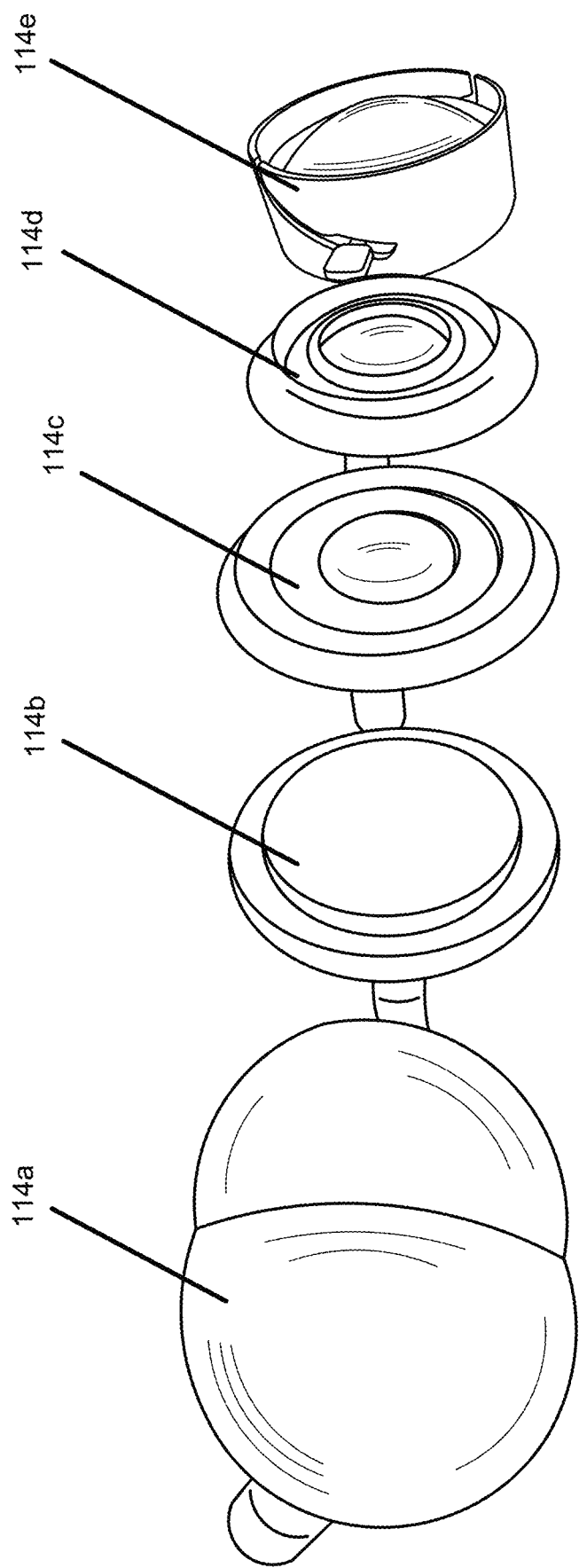
FIG. 6 illustrates a plurality of lenses for the signal transmission device.

FIG. 6 illustrates a plurality of lenses 114a-114e. Each lens 114a-114e is configured to attach to the signal transmission device 122 and to focus the radar signals transmitted from the signal transmission device 122 on a target area. Each lens 114a-114e is attachable to the signal transmission device 122 by screwing onto or snap-fitting onto an exterior housing of the signal transmission device 122 or by using one or more clamps, screws, bolts, etc. The beam of radar signals transmitted from the signal transmission device 122 is a combination of the antenna effects and the lens effects. Both may be adjusted to optimize the radar signal transmission.

Each lens 114a-114e narrows the dispersion of the radar signals transmitted from the signal transmission device 122 so that a higher density of radar signals are directed to the target area for measuring vital signs such as respiration rate, depth of respiration, or heart rate. By increasing the density of the radar signals, the signal-to-noise ratio is increased, cross-talk and background scatter is reduced, and the quality of the vital sign measurement is improved.

As an example, the radar signals transmitted from the signal transmission device 122 are dispersed at 120 degrees, and each lens can narrow the dispersion of the radar signals from 120 degree to 40 degrees, 30 degrees, 20 degrees, etc. As a further example, the lenses 114a-114e are configured to collimate the radar signals transmitted from the signal transmission device 122 so that the radar signals are focused on the target area. By focusing the dispersion of the radar signals, the lenses 114a-114e reduce noise and improve signal strength.

In some examples, the lenses 114a-114e are replaceable with another so that each lens 114a-114e can provide a different focus (e.g., 40 degrees, 30 degrees, 20 degrees, etc.) for the radar signals transmitted from the signal transmission device 122. Thus, a particular lens 114a-114e can be selected as may be needed or desired for a particular application to provide a desired focus for the radar signals from the signal transmission device 122.

Figure 7:
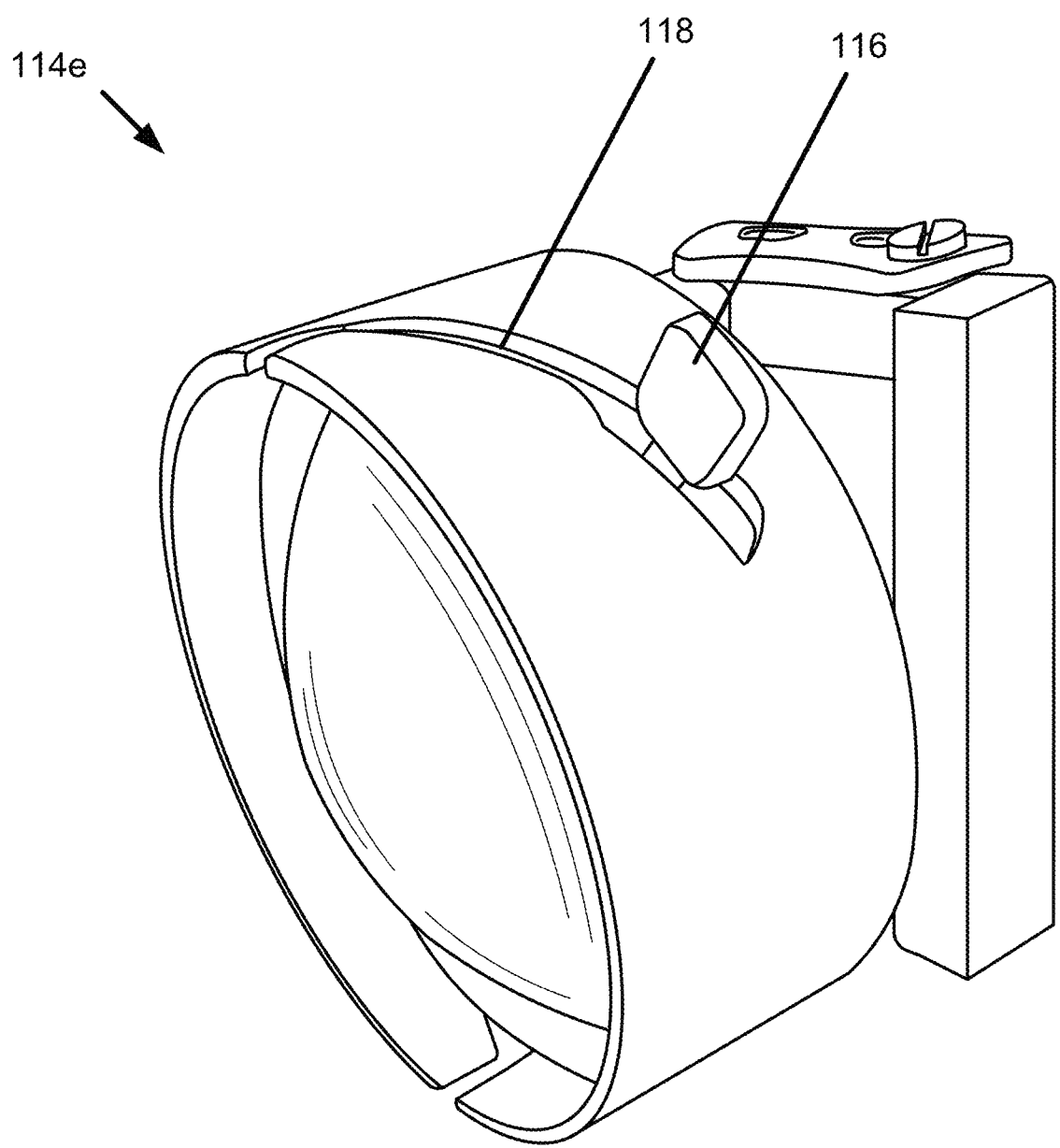
FIG. 7 illustrates an adjustable lens for the signal transmission device.

FIG. 7 illustrates an adjustable lens 114e for the signal transmission device 122. The adjustable lens 114e can adjust the focus of the radar signals as needed. For example, the adjustable lens 114e can adjust the focus of the radar signals from a large dispersion (e.g., 120 degrees) to a smaller, more focused dispersion (e.g., 40 degrees, 30 degrees, 20 degrees, etc.). In some examples, the adjustable lens 114e automatically moves to locate the strongest signal in the target area. In alternative examples, the adjustable lens 114e can include a handle 116 that is slidable through a groove 118 for adjusting the focus of the radar signals.

In the examples illustrated in FIGS. 6 and 7, the lenses 114a-114e are illustrated as molded from an opaque plastic material. In other examples, the lenses 114a-114e are molded from a clear plastic material. In examples where a clear plastic material is used, the aiming device 124 can be located behind the lens to emit a visible light through the lens for visually indicating the target area in the direction of the transmission of the radar signals. In certain examples, lenses 114a-114e are used without or separately from the aiming device 124.

Figure 8:
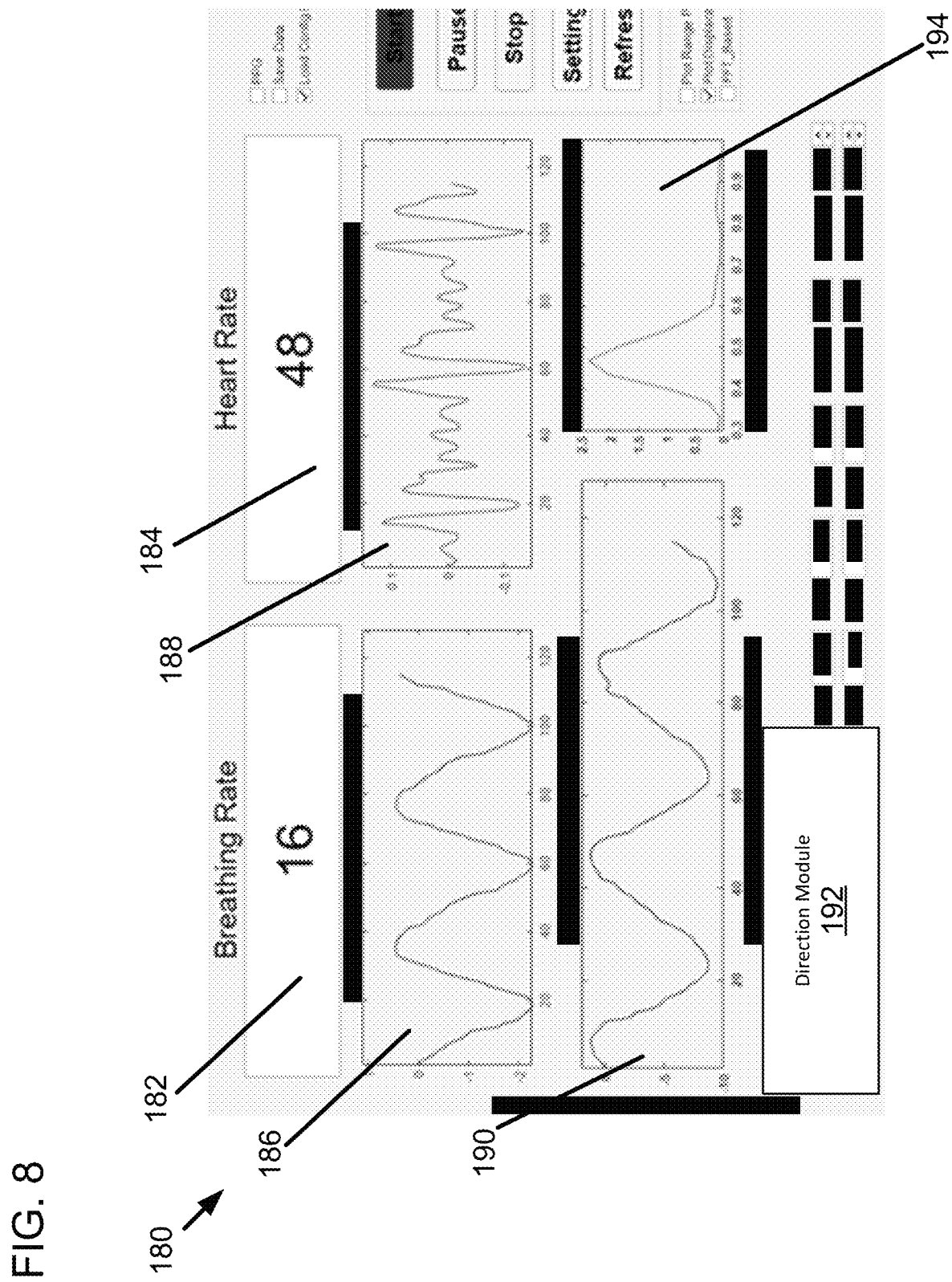
FIG. 8 illustrates a user interface for the monitoring device.

FIG. 8 illustrates a user interface 180 for the monitoring device 102. As shown in FIG. 8, the user interface 180 includes a display 182 for the breathing rate (i.e., respiration rate) and a display 184 for the heart rate determined by the monitoring device 102. The user interface 180 further includes a display 190 for the chest displacement (i.e., depth of respiration) determined by the monitoring device 102. The user interface 180 may provide other information including a quality indication, a range indication, an uncertainty indication, a signal-to-noise indication, and a patient movement indication. The patient movement indication may be adapted to a Braden mobility scale related to probability of bedsores occurring.

Further, in addition to the visual indication provided by the aiming device 124 on the target area, the user interface 180 also displays an amplitude module 186 that indicates the time-varying signal from which features such as the breathing rate (i.e., respiration rate) and depth of respiration are extracted, and an amplitude module 188 that indicates the time-varying heart signal from which features such as the heart rate are extracted. In the example of FIG. 8, the amplitude modules 186, 188 display the breathing rate and heart rate amplitudes, respectively, as waveforms on the user interface 180. In alternative examples, the amplitude modules 186, 188 display the breathing rate and heart rate amplitudes, respectively, as numerical values. The breathing rate and heart rate amplitudes displayed on the user interface 180 provide further indication that the monitoring device 102 is active and sensing one or more vital signs.

The user interface 180 further includes an indicator module 192 to provide user guidance for a need to move the signal transmission device 122 to improve signal strength. For example, the indicator module 192 can provide user guidance on movement in the azimuth and elevation directions for the signal transmission device 122 to improve the signal strength.

Additionally, the user interface 180 includes a range profile indicator 194 that indicates a range of the reflected radar signals received by the signal transmission device 122. The range profile indicator 194 ensures that the breathing rate and heart rate are determined based on data from reflected radar signals that are within a predetermined range of the monitoring device 102, and accordingly ensures the veracity of the vital sign measurements.

Data such as respiration rate can be stored on the monitoring device 102. Further, the data can be communicated by the monitoring device 102 to a remote computing device such as the data management system 108 for storage in an electronic medical record of the patient.

Figure 9:
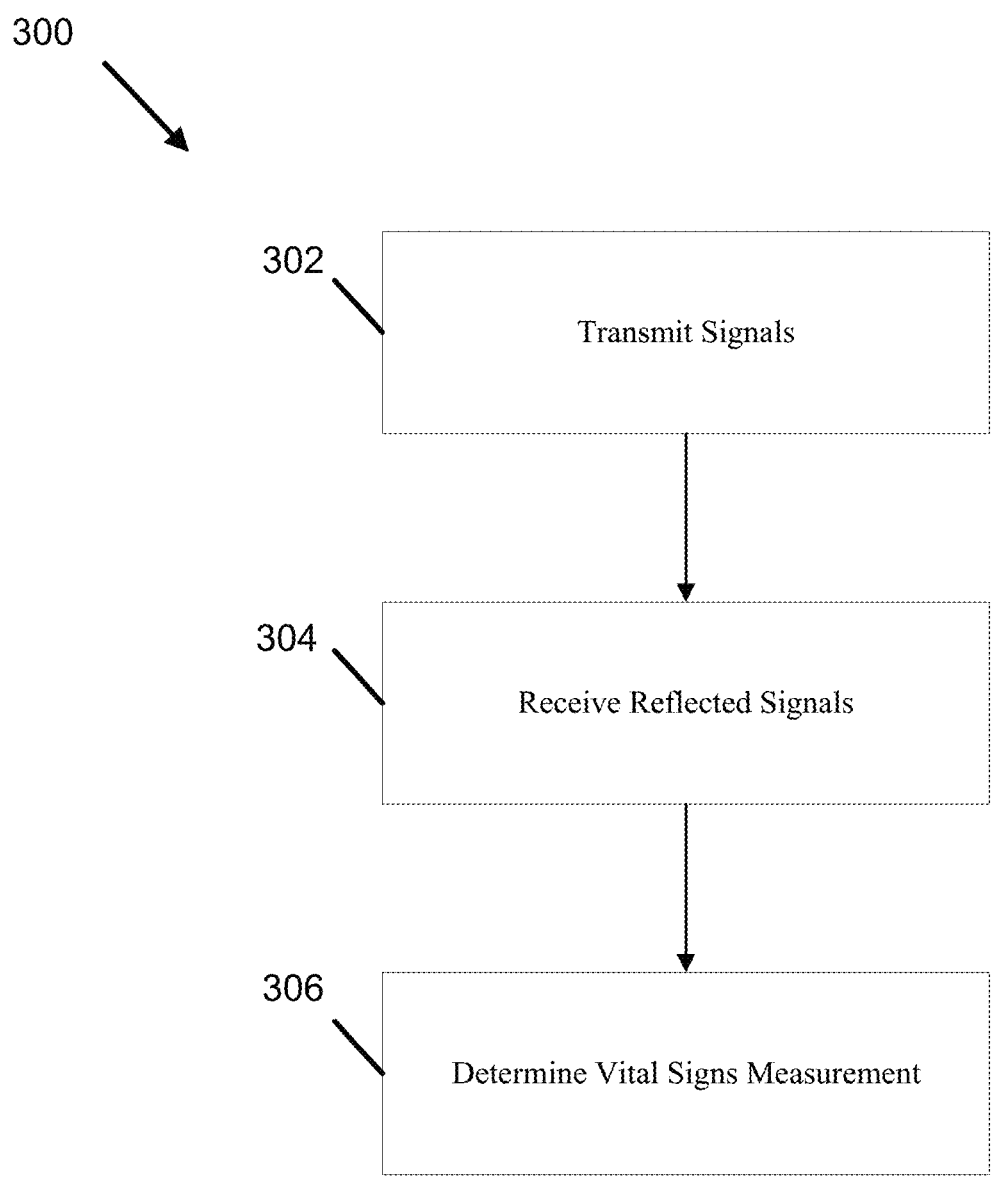
FIG. 9 illustrates a method of acquiring a vital sign measurement using a radar signal transmission.

FIG. 9 illustrates a method 300 of acquiring a vital sign measurement. In one example embodiment, the method 300 is implemented by the signal analysis device 120. In an alternative example embodiment, the method 300 is implemented by the signal transmission device 122.

As shown in FIG. 9, the method 300 includes a step 302 of transmitting radar signals. As described above, the monitoring device 102 includes a transmitter unit 126 having one or more signal transmitters 144 for producing radar signals and one or more transmitting antennas 146 for transmitting the radar signals toward a target area such as the subject arrangement area 104 where a subject S is located (see, for example, FIG. 1).

Next, the method 300 includes a step 304 of receiving reflected radar signals. As described above, the monitoring device 102 further includes a receiver unit 128 having one or more signal receivers 148 and one or more receiving antennas 150 for receiving the radar signals reflected from objects such as the subject S in the subject arrangement area 104.

Next, the method 300 includes a step 306 of determining a vital sign measurement based on data from the reflected radar signals. An algorithm is stored in the storage device of the signal analysis device 120 and is used to determine the vital sign measurement based on the raw data collected from the reflected radar signals. In an alternative example embodiment, the algorithm is stored in the storage unit 138 of the signal transmission device 122. The raw data may also be transmitted to an external computer for analysis and/or addition to a database of signals. The raw data may also be clinically annotated with diagnoses and outcomes.

The data used by the algorithm to determine the vital sign measurement includes changes in the frequency of the reflected radar signals, caused by the Doppler effect, due to an object moving toward or away from the signal transmission device 122. For example, changes in the frequency of the reflected radar signals caused by the chest of the subject S moving up and down during breathing can be used by the algorithm to determine respiration rate, depth of respiration, or heart rate. By performing the method 300, the monitoring device 102 determines one or more vital sign measurements of the subject S without having to contact the subject S.

In some examples, the method 300 uses at least one of detection theory, pattern classification, neural networks, artificial intelligence, cloud-based computing, and image processing to determine a vital sign measurement. The algorithm used by the method 300 may receive inputs for patient ethnographics including gender, age, weight, race, and medical history.

In further examples, the method 300 uses at least one of Fourier transform, fast Fourier transform (FFT), short Fourier transform (SFT), fast Hartley transform, wavelet analysis, Gabor transform, or Wigner distribution function (WVD) to determine a vital sign measurement. For example, the Fourier transform may be used to determine the frequency content of a signal. If the frequency content is within an expected range (e.g., 4 to 30 beats for respiration rate), then the signal is accepted. Fast Fourier transforms are a computationally efficient method of applying Fourier transforms and fast Hartley transforms are efficient methods of determining the frequency content of a signal.

Wavelet, Gabor, and Wigner methods are appropriate when both temporal and frequency content are needed (as typical Fourier and Hartley transforms with high frequency content have low temporal resolution). Conversion of the raw data to the frequency domain allows characterization of the raw data, for example, relative and phase amplitudes of harmonics. Stridor, rales, and other pulmonary issues have characteristic sounds and hence characteristic frequencies that modulate the signal. The ratio of amplitudes of different harmonics provides guidance on the quality of the respiration effort (e.g., how clean or unhampered the respiration effort is). For example, two patients can have the same respiration rate (e.g., at 12 breaths/min), but one patient's respiration can be labored and the waveform will appear jagged which indicates difficult breathing. The quality of the patient's respiration can be assessed along with the amplitude of the breath as the chest inflects and deflects.

The method 300 may include further steps to subtract background noise, and thereby improve the quality of the vital sign measurement. In one example, the method 300 uses range filters to remove reflected radar signals that are outside a predetermined range of distance when determining the vital sign measurement. For example, range filters can ensure that only reflected radar signals that travel between the monitoring device 102 and the subject arrangement area 104 are analyzed to determine the vital sign measurement.

In another example, the method 300 uses time and frequency-domain filters to remove reflected radar signals outside a predetermined frequency range when determining the vital sign measurement. For example, the received waveform may be correlated with the expected shape of a known respiration waveform to discriminate against non-respiratory signals before determining the respiratory rate. Clutter filters may be used to subtract out ambient background reflections. Low-pass Doppler filters can be used to remove signals from ambulating persons (e.g., nurses) while preserving the signals from patients lying in bed. The filter shapes and frequencies preferably vary with patient demographics and can be adapted to the patient. For example, the acceptable range for respiration rate is much higher for neonatal patients than for adults and the width of the breaths is smaller, so the frequency content of the physiological modulation of the radar signal is higher than would be expected for an adult. Once the physiological signal is found, the time- and frequency-domain filters adapt to match the characteristics of that patient, which allows the system to further ignore noise. For example, a patient with a fast inhalation cycle has more energy in higher-frequency components than a patient with the same respiration rate and a slower inhalation cycle.

In another example, the method 300 uses a Doppler filter to accept only reflected radar signals within a predetermined frequency range when determining the vital sign measurement. For example, objects having no motion such as a bed or chair, and hence no Doppler signal, are removed when performing the method 300 so that only a moving object is analyzed. A high-pass output of a Doppler filter can be used to reject the motionless objects. Alternatively, a clutter filter is used to subtract a previous output from a high-pass Doppler filter from a new radar return. Objects identified as moving beyond a predetermined threshold are rejected or ignored such as, for example, a nurse walking into the room. The Doppler filter has a low-pass component that ignores high-frequency signals from ambulating persons (e.g., the nurse). The net is a band pass filter that ignores high-motion and no-motion objects.

In some examples, the method 300 uses a micro-Doppler effect to identify a target area (e.g., the subject S lying in the support device 106) and guide the radar signal transmission. For example, respiration can create an expected phase change of about $x*2\pi/\lambda$, where x is the chest displacement and $\lambda$ is the wavelength of the transmitted signal, and this signal is on the order of about 0.5 mm at a frequency of about 60 GHz. A targeting algorithm can scan for a target area with a periodic micro-Doppler variation of amplitude approximately 0.5 mm.

In further examples, the method 300 uses azimuth and elevation filters to remove reflected radar signals outside a predetermined direction when determining the vital sign measurement. For example, reflected radar signals that are outside of an azimuth or elevation range where the subject S is located are removed by the azimuth and elevation filters.

In another example, the method 300 uses frequency chirping to transmit the radar signals. In some examples, the method 300 transmits the radar signals using frequency chirping at predetermined time intervals of 50 milliseconds. In further examples, the method 300 uses millimeter waves in a spectrum between about 30 GHz and about 300 GHz.

Figure 10:
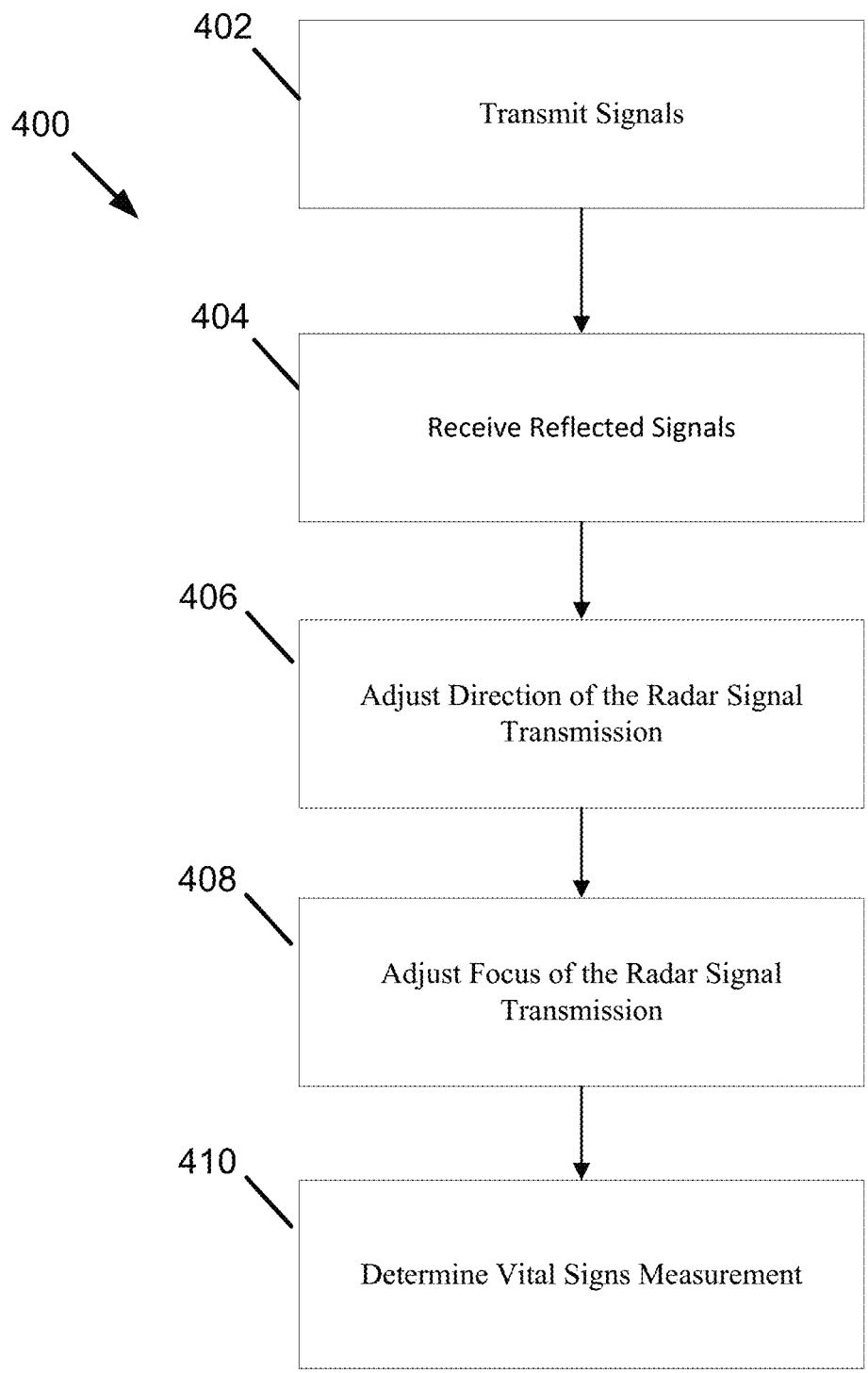
FIG. 10 illustrates a method of adjusting a direction and focus of a radar signal transmission for acquiring a vital sign measurement.

FIG. 10 illustrates a method 400 of adjusting a direction and focus of a radar signal transmission for acquiring a vital sign measurement. For example, even when a medical professional is able to see where the radar signal transmission is pointed to by using the aiming device 124, obtaining an optimal signal strength for measuring a vital sign such as respiration rate may be difficult because the medical professional is often unable to see the area on the chest having the most robust movement in the direction of the radar signal transmission. Therefore, the method 400 may further improve the quality of the vital sign measurement.

In one example embodiment, the method 400 is implemented by the signal transmission device 122. In an alternative example embodiment, the method 400 is implemented by the signal analysis device 120.

The method 400 includes a step 402 of transmitting radar signals in a direction toward a target area such as the chest of the subject S. As described above, the aiming device 124 can be used to provide a course aim for directing the radar signal transmission from the monitoring device 102 by optically illuminating the center of the radar signal transmission so that a medical professional can view where the radar signal transmission is pointed. The visual marker from the aiming device 124 provides an indicator to the medical professional that the monitoring device 102 is active and sensing a vital sign such as respiration rate.

Next, the method 400 includes a step 404 of receiving reflected signals. In some examples, the amplitude of the reflected signals is displayed on the user interface 180 of the monitoring device 102 as a further indicator that the monitoring device 102 is active and sensing one or more vital signs such as respiration rate. In some examples, the reflected signals are used to determine a target nominal range. In one example, the amplitude of the vital signs signal is displayed as a waveform on the user interface 180. In another example, the amplitude of the vital signs signal is displayed as a numerical value on the user interface 180.

Next, the method 400 includes a step 406 of adjusting the direction of the radar signal transmission. The direction of the radar signal transmission can be adjusted by using an amplitude of reflected radar signals, and can be adjusted in both the azimuth and elevation directions. In one example embodiment, the direction of the transmission of radar signals is adjusted electronically by the phased array of the signal transmission device 122*a*. In an alternative example embodiment, the direction of the radar signal transmission is adjusted by mechanically steering the pivoted support 130 of the signal transmission device 122*b*.

Next, the method 400 includes a step 408 of adjusting a focus of the radar signal transmission. In one example, the focus of the radar signal transmission is adjusted electronically by the phased array of the signal transmission device 122*a*. In an alternative example, the focus of the radar signal transmission is adjusted by placing a lens 114*a*-114*e* over the signal transmission device 122*b*. In a further example, the lens is an adjustable lens 114*e* that automatically adjusts the focus of the radar signal transmission or that can be manually manipulated to further adjust the focus of the radar signal transmission.

Next, the method 400 includes a step 410 of determining a vital sign measurement based on data from the reflected radar signals. An algorithm stored in the storage device of the signal analysis device 120 or in the storage unit 138 of the signal transmission device 122 is used to determine the vital sign measurement based on data collected from the reflected radar signals. The data used by the algorithm to calculate the vital sign measurement includes changes in the frequency of the reflected radar signals, caused by the Doppler effect, due to an object moving toward or away from the signal transmission device 122. For example, changes in the frequency of the reflected radar signals caused by the chest of the subject S moving up and down during breathing can be used by the algorithm to determine respiration rate, depth of respiration, or heart rate. By performing the method 400, the monitoring device 102 determines one or more vital sign measurements of the subject S without having to contact the subject S.

Figure 11:
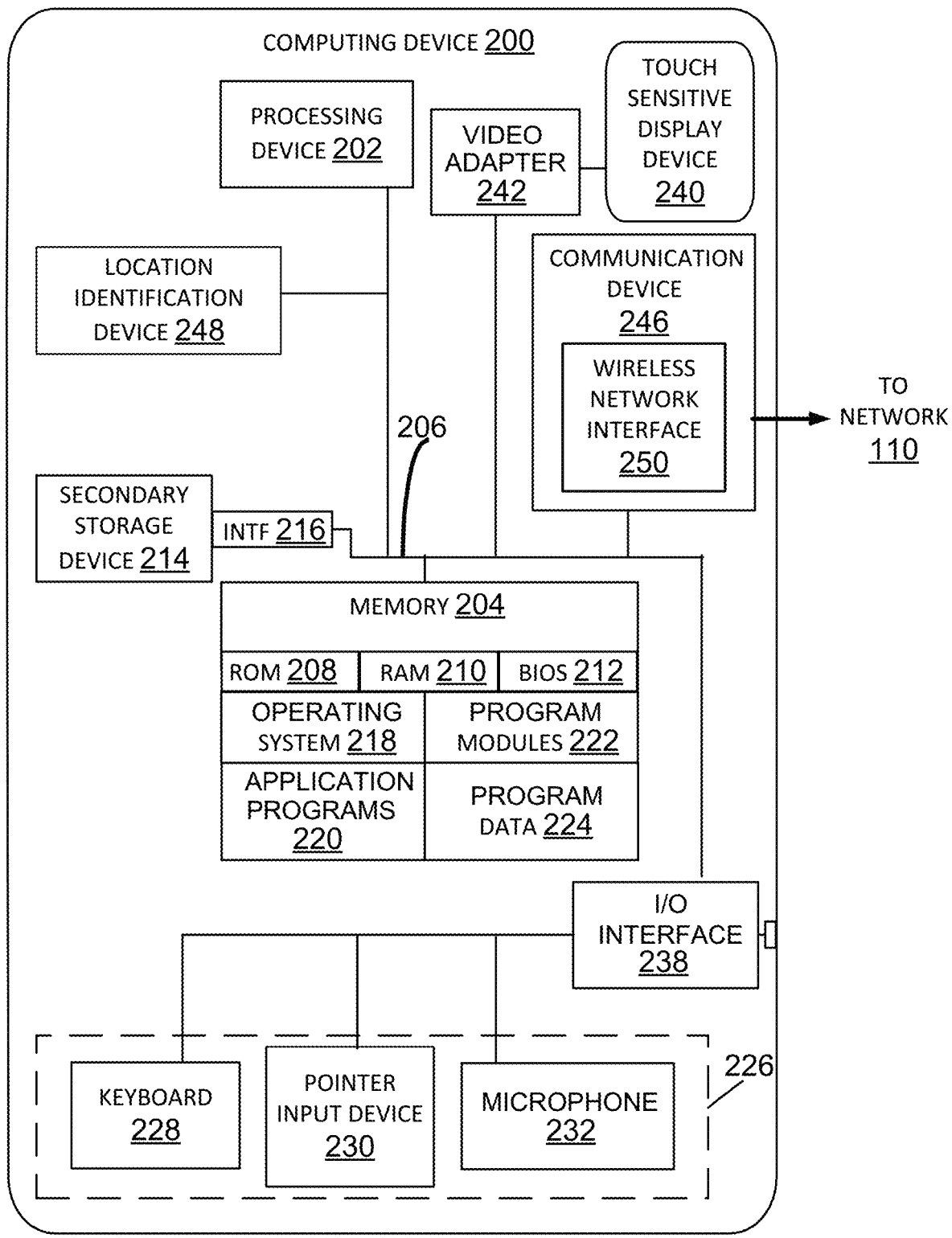
FIG. 11 illustrates an exemplary architecture of a computing device that can be used to implement aspects of the present disclosure.

FIG. 11 illustrates an exemplary architecture of a computing device 200 which can be used to implement aspects of the present disclosure, including the monitoring device 102 and the data management system 108, and will be referred to herein as the computing device 200. The computing device 200 is used to execute the operating system, application programs, and software modules (including the software engines) described herein. The monitoring device 102 and the data management system 108 can include all or some of the elements described with reference to FIG. 11, with or without additional elements.

The computing device 200 includes, in some examples, at least one processing device 202, such as a central processing unit (CPU). A variety of processing devices are available from a variety of manufacturers, for example, Intel or Advanced Micro Devices. In this example, the computing device 200 also includes a system memory 204, and a system bus 206 that couples various system components including the system memory 204 to the processing device 202. The system bus 206 is one of any number of types of bus structures including a memory bus, or memory controller; a peripheral bus; and a local bus using any of a variety of bus architectures.

The system memory 204 may include read only memory 208 and random access memory 210. A basic input/output system 212 containing the basic routines that act to transfer information within the computing device 200, such as during start up, is typically stored in the read only memory 208.

The computing device 200 also includes a secondary storage device 214 in some embodiments, such as a hard disk drive, for storing digital data. The secondary storage device 214 is connected to the system bus 206 by a secondary storage interface 216. The secondary storage devices and their associated computer readable media provide nonvolatile storage of computer readable instructions (including application programs and program modules), data structures, and other data for the computing device 200.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 214 or memory 204, including an operating system 218, one or more application programs 220, other program modules 222, and program data 224.

In some embodiments, the computing device 200 includes input devices to enable a user to provide inputs to the computing device 200. Examples of input devices 226 include a keyboard 228, a pointer input device 230, a microphone 232, and a touch sensitive display 240. Other embodiments include other input devices. The input devices are often connected to the processing device 202 through an input/output interface 238 that is coupled to the system bus 206. These input devices 226 can be connected by any number of input/output interfaces, such as a parallel port, serial port, game port, or a universal serial bus. Wireless communication between input devices and the input/output interface 238 is possible as well, and includes infrared, BLUETOOTH® wireless technology, 802.11a/b/g/n, cellular, or other radio frequency communication systems in some possible embodiments.

In one example embodiment, a touch sensitive display 240 is connected to the system bus 206 via an interface, such as a video adapter 242. The touch sensitive display 240 includes touch sensors for receiving input from a user when the user touches the display. Such sensors can be capacitive sensors, pressure sensors, or other touch sensors. The sensors detect contact with the display, and also the location and movement of the contact over time. For example, a user can move a finger or stylus across the screen to provide written inputs. The written inputs are evaluated and, in some embodiments, converted into text inputs.

In addition to the touch sensitive display 240, the computing device 200 can include various other peripheral devices (not shown), such as speakers or a printer.

The computing device 200 further includes a communication device 246 configured to establish communication across a network. In some embodiments, when used in a local area networking environment or a wide area networking environment (such as the Internet), the computing device 200 is typically connected to the network through a network interface, such as a wireless network interface 250. Other possible embodiments use other wired and/or wireless communication devices. For example, some embodiments of the computing device 200 include an Ethernet network interface, or a modem for communicating across the network.

In yet other embodiments, the communication device 246 is capable of short-range wireless communication. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The computing device 200 typically includes at least some form of computer-readable media. Computer readable media includes any available media that can be accessed by the computing device 200. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 200. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device 200 is an example of programmable electronics, which may include one or more computing devices, and when multiple computing devices are included, such computing devices can be coupled together with a suitable data communication network so as to collectively perform the various functions, methods, or operations disclosed herein.

The computing device 200 can include a location identification device 248. The location identification device 248 is configured to identify the location or geolocation of the computing device 200. The location identification device 248 can use various types of geolocating or positioning systems, such as network-based systems, handset-based systems, SIM-based systems, Wi-Fi positioning systems, and hybrid positioning systems. Network-based systems utilize service provider's network infrastructure, such as cell tower triangulation. Handset-based systems typically use the Global Positioning System (GPS). Wi-Fi positioning systems can be used when GPS is inadequate due to various causes including multipath and signal blockage indoors. Hybrid positioning systems use a combination of network-based and handset-based technologies for location determination, such as Assisted GPS.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

The systems and method described herein result in a significant technical advantage. For example, the monitoring device 102 more efficiently captures vital sign measurements including respiration rate, depth of respiration, and heart rate. Additionally, the monitoring device 102 determines vital sign measurements more accurately and in less time. Finally, the captured vitals can be more efficiently displayed.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features.

Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A patient monitoring device, comprising:
   a transceiver for transmitting millimeter wave signals toward a target area and receiving reflected millimeter wave signals from the target area;
   a replaceable lens attached to the transceiver, the replaceable lens being configured to collimate the millimeter wave signals transmitted from the transceiver, and the replaceable lens including a slidable handle for adjusting a focus of the millimeter wave signals between large and small dispersions; and
   a signal analysis device having a processing device and at least one non-transitory computer readable data storage device storing instructions, that when executed by the processing device, cause the patient monitoring device to:
   transmit the millimeter wave signals;
   receive the reflected millimeter wave signals; and
   determine a non-contact vital sign measurement based on the reflected millimeter wave signals.

2. The patient monitoring device of claim 1, further comprising an aiming device to optically illuminate a center of the millimeter wave signals transmitted on the target area.

3. The patient monitoring device of claim 1, wherein the millimeter wave signals are transmitted by frequency chirping at a predetermined time interval.

4. The patient monitoring device of claim 1, wherein the transceiver includes a phased array configured to electronically adjust the direction of the millimeter wave signals without mechanically moving the transceiver.

5. The patient monitoring device of claim 1, wherein the non-contact vital sign measurement is respiration rate, depth of respiration, quality of respiration, or heart rate.

6. The patient monitoring device of claim 5, wherein the non-contact vital sign measurement is used to predict patient decline.

7. The patient monitoring device of claim 1, wherein the transceiver identifies a patient for determining the vital sign measurement by detecting a beacon signal from a tag attached to the patient.

8. A patient monitoring device, comprising:
   a transceiver configured to direct a millimeter wave signal transmission toward a target area and to receive reflected millimeter wave signals from the target area;
   a replaceable lens attached to the transceiver, the replaceable lens being configured to collimate the millimeter wave signal transmission from the transceiver, and the replaceable lens including a slidable handle for adjusting a focus of the millimeter wave signal transmission between large and small dispersions; and
   a signal analysis device programmed to determine a respiration rate based on the reflected millimeter wave signals.

9. The patient monitoring device of claim 8, further comprising an aiming device configured to optically illuminate a center of the millimeter wave signal transmission on the target area.

10. A method of acquiring a vital sign measurement comprising:
    transmitting millimeter wave signals toward a target area;
    receiving reflected millimeter wave signals;
    adjusting a direction of the millimeter wave signals;
    collimating the millimeter wave signals transmitted toward the target area using a replaceable lens;
    providing a slidable handle on the replaceable lens for adjusting a focus of the millimeter wave signals between large and small dispersions; and
    determining a vital sign measurement based on the reflected millimeter wave signals.

11. The method of claim 10, further comprising providing an indication of where to move the direction of the millimeter wave signals to improve signal strength.

12. The method of claim 10, wherein the direction of the millimeter wave signals is automatically adjusted based on the reflected signals.

13. The method of claim 10, further comprising using micro-Doppler effect to identify the target area and guide the millimeter wave signals.

14. The method of claim 10, further comprising using a Doppler filter to filter the reflected millimeter wave signals in a predetermined frequency range when determining the vital sign measurement.

15. The method of claim 10, further comprising using pattern recognition to extract physiological data from the reflected millimeter wave signals.

16. The method of claim 10, further comprising use of frequency domain analysis or time-domain analysis to extract physiological data from the reflected millimeter wave signals.

17. The method of claim 10, further comprising displaying the vital sign measurement extracted from the reflected millimeter wave signals.

* * * * *